(12) United States Patent
Govari et al.

(10) Patent No.: US 11,638,610 B2
(45) Date of Patent: May 2, 2023

(54) USING FORCE SENSOR TO GIVE ANGLE OF ULTRASOUND BEAM

(71) Applicant: BIOSENSE WEBSTER (ISRAEL) LTD., Yokneam (IL)

(72) Inventors: Assaf Govari, Haifa (IL); Andres Claudio Altmann, Haifa (IL); Dimitry Volkinshtein, Zichron Yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 412 days.

(21) Appl. No.: 16/266,318

(22) Filed: Feb. 4, 2019

(65) Prior Publication Data

US 2019/0167358 A1 Jun. 6, 2019

Related U.S. Application Data

(62) Division of application No. 14/974,731, filed on Dec. 18, 2015, now Pat. No. 10,231,789.

(51) Int. Cl.
*A61B 34/00* (2016.01)
*A61B 34/20* (2016.01)
(Continued)

(52) U.S. Cl.
CPC .............. *A61B 34/20* (2016.02); *A61B 5/283* (2021.01); *A61B 5/318* (2021.01); *A61B 5/6885* (2013.01);
(Continued)

(58) Field of Classification Search
CPC ......... A61B 34/20; A61B 5/318; A61B 5/283; A61B 5/6885; A61B 8/0858; A61B 8/0883; A61B 8/12; A61B 8/4466; A61B 8/1492; A61B 2034/2051; A61B 2090/2065; A61B 2098/3784; A61B 2017/00106;
(Continued)

(56) References Cited

U.S. PATENT DOCUMENTS 6,226,542 B1 5/2001 Reisfeld
6,301,496 B1 10/2001 Reisfeld
(Continued)

FOREIGN PATENT DOCUMENTS

CA 2492283 C 12/2013
EP 2 130 508 12/2009
(Continued)

OTHER PUBLICATIONS

European Search Report dated May 19, 2017 from corresponding European Patent Application No. 16204794.8.

*Primary Examiner* — Keith M Raymond
*Assistant Examiner* — Adam D. Kolkin
(74) *Attorney, Agent, or Firm* — Dergosits & Noah LLP; Todd A. Noah

(57) ABSTRACT

Catheterization is carried out by inserting a probe into a cavity in a body of a subject. The probe has a contact force, a transmitter, a receiver, and an ultrasound transducer in its distal segment. After navigating the probe into contact with a target in a wall of the cavity using the contact force sensor, a desired contact force is established and maintained between the probe and the target. Responsively to readings by the receiver of signals from the transmitter, the distal end of the probe is oriented orthogonally to the target.

9 Claims, 4 Drawing Sheets

(51) Int. Cl.
| | | |
|---|---|---|
| *A61B 5/00* | (2006.01) | |
| *A61B 8/00* | (2006.01) | |
| *A61B 5/283* | (2021.01) | |
| *A61B 5/318* | (2021.01) | |
| *A61B 8/08* | (2006.01) | |
| *A61B 8/12* | (2006.01) | |
| *A61B 18/14* | (2006.01) | |
| *A61B 90/00* | (2016.01) | |
| *A61B 17/22* | (2006.01) | |
| *A61B 18/00* | (2006.01) | |
| *A61B 17/00* | (2006.01) | |

(52) U.S. Cl.
CPC .......... *A61B 8/0858* (2013.01); *A61B 8/0883* (2013.01); *A61B 8/12* (2013.01); *A61B 8/4466* (2013.01); *A61B 18/1492* (2013.01); *A61B 2017/00106* (2013.01); *A61B 2017/22005* (2013.01); *A61B 2018/00357* (2013.01); *A61B 2018/00577* (2013.01); *A61B 2018/00815* (2013.01); *A61B 2018/00982* (2013.01); *A61B 2034/2051* (2016.02); *A61B 2090/065* (2016.02); *A61B 2090/3784* (2016.02)

(58) Field of Classification Search
CPC .......... A61B 2017/22005; A61B 2018/00357; A61B 2018/00577; A61B 2018/00815; A61B 2018/00982
See application file for complete search history.

(56) References Cited

U.S. PATENT DOCUMENTS

| | | | |
|---|---|---|---|
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,306,593 B2 * | 12/2007 | Keidar | A61B 34/20 606/41 |
| 7,536,218 B2 | 5/2009 | Govari et al. | |
| 7,756,576 B2 | 7/2010 | Levin | |
| 8,333,704 B2 | 12/2012 | Anthony et al. | |
| 8,374,670 B2 | 2/2013 | Selkee | |
| 8,545,409 B2 | 10/2013 | Sliwa et al. | |
| 2007/0167804 A1 * | 7/2007 | Park | A61B 8/12 600/459 |
| 2008/0039742 A1 * | 2/2008 | Hashimshony | A61B 5/0071 600/587 |
| 2009/0093806 A1 | 4/2009 | Govari et al. | |
| 2011/0130648 A1 | 6/2011 | Beeckler et al. | |
| 2011/0288544 A1 | 11/2011 | Verin et al. | |
| 2012/0265070 A1 | 10/2012 | Sliwa et al. | |
| 2014/0100563 A1 | 4/2014 | Govari et al. | |
| 2014/0171942 A1 | 6/2014 | Werneth et al. | |
| 2014/0187916 A1 * | 7/2014 | Clark | A61B 5/065 600/424 |
| 2014/0276692 A1 | 9/2014 | Sliwa | |
| 2015/0018679 A1 | 1/2015 | Endo | |
| 2019/0254562 A1 | 8/2019 | Clark | |

FOREIGN PATENT DOCUMENTS

| | | |
|---|---|---|
| EP | 2 749 211 | 7/2014 |
| EP | 2696774 B1 | 8/2018 |
| EP | 2380180 B1 | 11/2019 |
| JP | 2005199072 A | 7/2005 |
| JP | 2009291616 A | 12/2009 |
| JP | 2013504398 A | 2/2013 |
| JP | 2014128680 A | 7/2014 |
| JP | 2014517737 A | 7/2014 |
| WO | WO96/05768 A1 | 2/1996 |
| WO | WO 2011/033421 | 3/2011 |

* cited by examiner

USING FORCE SENSOR TO GIVE ANGLE OF ULTRASOUND BEAM

CROSS REFERENCE TO RELATED APPLICATIONS

This application is a divisional application of U.S. patent application Ser. No. 14/974,731, filed Dec. 18, 2015, the entire contents of which are hereby incorporated by reference.

BACKGROUND OF THE INVENTION

1. Field of the Invention

This invention relates to devices and methods for transferring energy to the body with a catheter. More particularly, this invention relates to devices and methods for operating a catheter by transferring mechanical, ultrasonic and electromagnetic energy to the body.

2. Description of the Related Art

Radiofrequency (RF) ablation is widely used for treating cardiac arrhythmias. RF ablation is commonly carried out by inserting a catheter through the patient's vascular system into the heart, and bringing the distal tip of the catheter into contact with the cardiac tissue at the site that is to be ablated. RF electrical current is then conducted through wires in the catheter to one or more electrodes at the tip of the catheter, which apply the RF energy to the myocardium. The RF energy is absorbed in the tissue, heating it to the point typically about 50°-60° C.) at which it permanently loses its electrical excitability. When this sort of procedure is successful, it creates non-conducting lesions in the cardiac tissue, which disrupt the abnormal electrical pathway causing the arrhythmia.

It is often difficult to determine the proper dosage of RF energy that should be applied in an ablation procedure in order to achieve the desired result. When the dosage is insufficient, the non-conducting lesion will not extend deeply enough through the heart wall to disrupt the abnormal conduction, so that arrhythmia may persist or return after the procedure is completed. On the other hand, excessive RF dosage may cause dangerous damage to the tissue at and around the ablation site. The proper RF dosage is known to vary from case to case depending on various factors, such as catheter geometry, thickness of the heart wall, quality of the electrical contact between the catheter electrode and the heart wall, and blood flow in the vicinity of the ablation site (which carries away heat generated by the RF energy).

In order to improve the precision and consistency of RF ablation procedures, attempts have been made to predict and control the ablation based on measurement of physiological parameters of relevance.

SUMMARY OF THE INVENTION

According to disclosed embodiments of the invention, a flexible cardiac catheter has an ablation electrode, a distal force sensor, radio-frequency transmitter and a radio-frequency receiver located at the distal end and the proximal end of a contact force sensor comprising a spring and an ultrasonic transducer into the distal tip of the catheter, on the axis of the tip. If there is no force on the tip, or if the force is parallel to the distal end axis, then the distal and proximal ends of the spring align, and the distal tip axis aligns with the axis of the distal portion of the catheter. If there is an asymmetrical force on the tip, then the two axes do not align. In all cases the orientation of the transducer, the beam emitted by the transducer may be calculated, and the alignment or nonalignment of the two axes may be determined. Once the axes are aligned, the ultrasound transducer may be operated in A-mode and the tension on the contact force sensor read in order to establish tissue structure and contact force for determination of ablation power and duration.

There is provided according to embodiments of the invention a method, which is carried out by inserting a probe into a cavity in a body of a subject, the probe has a contact force sensor, a transmitter, a receiver and an ultrasound transducer in the distal segment, The method is further carried out by navigating the probe into contact with a target in a wall of the cavity, and according to readings of the contact force sensor establishing a desired contact force between the probe and the target. Responsively to readings by the receiver of signals from the transmitter, the ultrasound transducer is positioned orthogonally to the target.

According to an aspect of the method, the contact force sensor is disposed between the transmitter and the receiver.

In one aspect of the method after orienting the ultrasound transducer the ultrasound transducer is activated to emit ultrasound signals, and echo signals returning from the emitted ultrasound signals are processed to determine a structure of the target.

According to still another aspect of the method, determining a structure of the target includes determining a thickness of the wall of the cavity.

Another aspect of the method is carried out responsively to the determined structure of the target by calculating ablation parameters, and activating an ablation electrode according to the ablation parameters to ablate the target.

According to a further aspect of the method, the distal segment has an axis of symmetry, the ultrasound transducer is centered on the axis of symmetry, and ultrasound signals emitted by the ultrasound transducer propagate along the axis of symmetry.

According to another aspect of the method the ultrasound transducer is offset from the axis of symmetry, and ultrasound signals emitted by the ultrasound transducer propagate parallel to the axis of symmetry.

According to an additional aspect of the method, the transmitter is a single frequency radiofrequency transmitter and the receiver has a single receiving coil.

According to another aspect of the method, the contact force sensor forms a joint between a proximal portion of the probe and the tip of the distal segment.

According to another aspect of the method, orienting the ultrasound transducer also includes aligning an axis of symmetry of the proximal portion with an axis of symmetry of the distal segment.

According to a further aspect of the method, orienting the ultrasound transducer is performed while maintaining the desired contact force.

There is further provided according to embodiments of the invention a flexible probe adapted for insertion into a body cavity of a patient. Within the probe are a transmitter and a position sensor for receiving signals from the transmitter to sense a position of the distal tip relative to the distal end of the probe, The probe has a resilient contact force sensor disposed between the transmitter and the position sensor, which couples the distal tip to the distal portion of the probe and is configured to deform in response to pressure exerted on the distal tip when the distal tip engages a wall of the body cavity. An ultrasound transducer is disposed in the distal portion for directing ultrasonic energy toward the wall, and a processor is linked to the position sensor for determining an angular deviation between the distal portion and the proximal portion of the probe.

According to still another aspect of the apparatus, the processor is operative to report that the distal tip is in alignment with the distal end of the probe.

According to another aspect of the apparatus, the processor is configured for activating the ultrasound transducer to emit ultrasound signals when the distal tip is in alignment with the distal end of the probe, and for processing echo signals returning from the emitted ultrasound signals to determine a thickness of the wall.

According to an additional aspect of the apparatus, an ablation electrode is disposed on the distal tip, and the processor is configured for calculating ablation parameters responsively to the thickness of the wall, and activating the ablation electrode according to the ablation parameters to ablate tissue in the wall.

According to still another aspect of the apparatus, the distal end has an axis of symmetry, and the ultrasound transducer is centered on the axis of symmetry, and ultrasound signals emitted by the ultrasound transducer propagate along the axis of symmetry.

According to yet another aspect of the apparatus the ultrasound transducer is offset from the axis of symmetry, and ultrasound signals emitted by the ultrasound transducer propagate parallel to the axis of symmetry.

According to a further aspect of the apparatus, the transmitter is a single frequency radiofrequency transmitter and the position sensor includes a single receiving coil.

According to one aspect of the apparatus, the contact force sensor forms a joint between the proximal portion of the probe and the distal end.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device couples to a second device, that connection may be through a direct connection, or through an indirect connection via other devices and connections.

Figure 1:
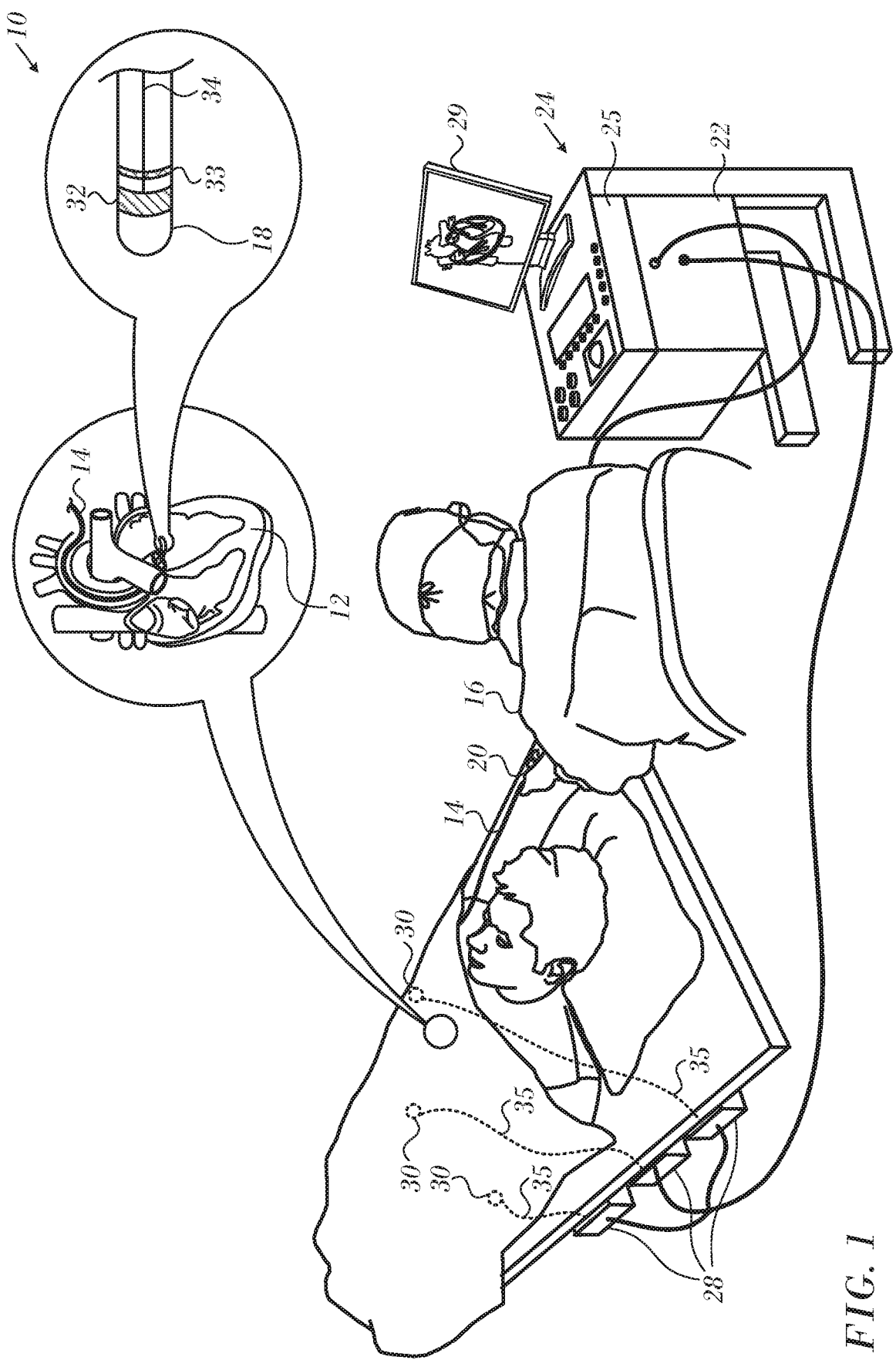
FIG. 1 is a pictorial illustration of a system for performing ablative procedures on a heart in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

During the procedure, contact force between the distal tip 18 or ablation electrode 32 and the wall of the chamber may be measured as described below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images that are described below.

Figure 2:
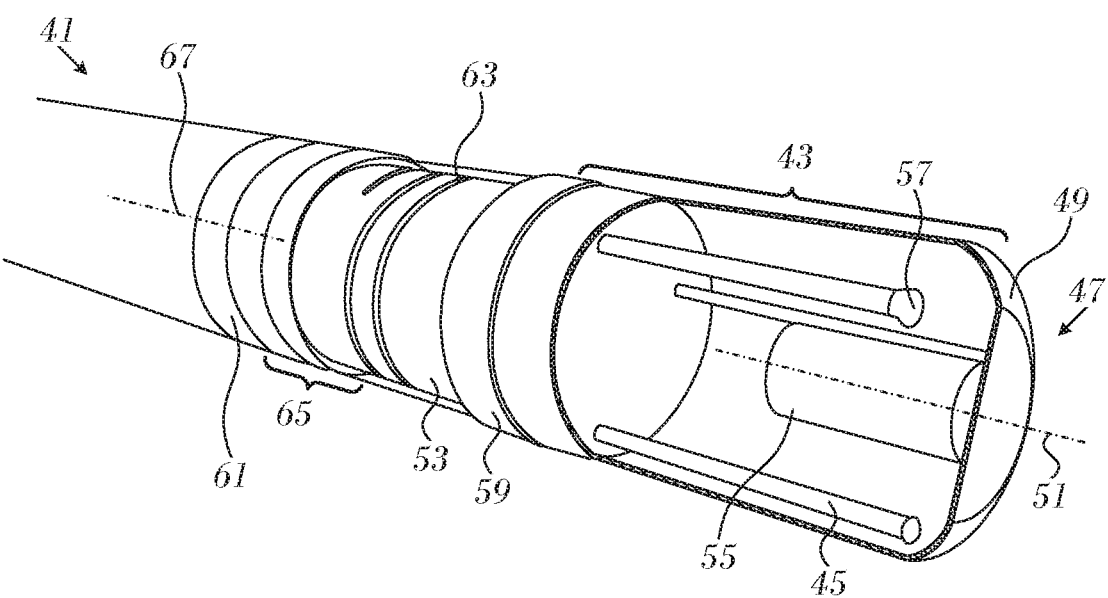
FIG. 2 is a partially cut away elevation of distal portion of a catheter in accordance with an embodiment of the invention.

Reference is now made to FIG. 2, which is a partially cut-away view of distal portion 41 of a catheter in accordance with an embodiment of the invention. The distal portion 41 has an end portion 43 that comprises an ablation electrode 45 mounted at tip 47. In this embodiment the ablation electrode 45 has a distal annular portion 49 centered about an axis of symmetry 51 for making contact with tissue. Contact is optimal when the axis of symmetry 51 is orthogonal to the tissue surface. A contact force sensor 53 is located proximal to the ablation electrode 45 and proximal to an ultrasonic transducer 55. In this embodiment the ultrasonic transducer 55 is partially enclosed by the ablation electrode 45, and the ultrasonic transducer 55 centered, so that its pulses transmit along the axis of symmetry 51. However, it is sufficient that there be a rigid alignment between the ablation electrode 45 and the ultrasonic transducer 55. For example, one or both of the ablation electrode 45 and the ultrasonic transducer 55 could be offset from the axis of symmetry 51, so long as the ultrasonic transducer 55 emits sound pulses parallel to the axis of symmetry 51. A temperature sensor 57 may be present in the distal portion 41 to monitor temperatures at the ablation site.

A receiver 59 in the end portion 43 may be a set of three coils that have a dual function. For a first function, the three coils act as a location detector for the distal end, by generating position-dependent signals from incident RF radiation produced by external field generating coils 28 (FIG. 1). The field generating coils 28 (typically also three) are fixed in a location pad that is positioned beneath a patient. Analysis of the position-dependent signal levels in the three receiving coils gives the location and the orientation of the distal end.

As a second function, the three coils generate force-dependent signals from the incident RF radiation produced by a transmitter 61. The two types of signals in the three coils—position-dependent and force dependent—may be easily distinguished by using different frequencies for the force transmitter and for the external RF radiators. Analysis of the force-dependent signals gives the magnitude of the force on the distal tip. The analysis also gives the orientation of the distal tip with respect to the axis of the proximal end of a spring 63 in the contact force sensor 53, i.e., the amount of bending of the helical spring.

The contact force sensor 53, comprising the spring 63 in the form of a double helix is disposed in the distal portion 41 and proximal to the ablation electrode 45. Proximal portion 65 of the contact force sensor 53 is disposed about a longitudinal axis 67. As the spring 63 is flexible, the longitudinal axis 67 is not necessarily aligned with the axis of symmetry 51. In other words the contact force sensor 53 acts as a joint between the tip 47 and the segment proximal to the contact force sensor 53. If there is no force on the tip 47, or if the force is parallel to the axis of symmetry 51, then the distal and proximal ends of the spring 63 align, and the axis of symmetry 51 aligns with the longitudinal axis 67 of the distal portion of the catheter (proximal to the contact force sensor 53). If there is an asymmetrical force on the tip, then the two axes do not align. In all cases the orientation of the transducer, the beam emitted by the transducer; may be calculated, and the alignment or nonalignment of the two axes may be determined.

The contact force sensor 53 is disposed between a paired radiofrequency receiver 59, which functions as a location detector and a single frequency transmitter 61. In this embodiment the receiver 59 is distal to the transmitter 61. However, they may be disposed in the opposite order. The transmitter 61 is a single frequency transmitter that is a simple dipole radiator, basically a single coil.

Figure 3:
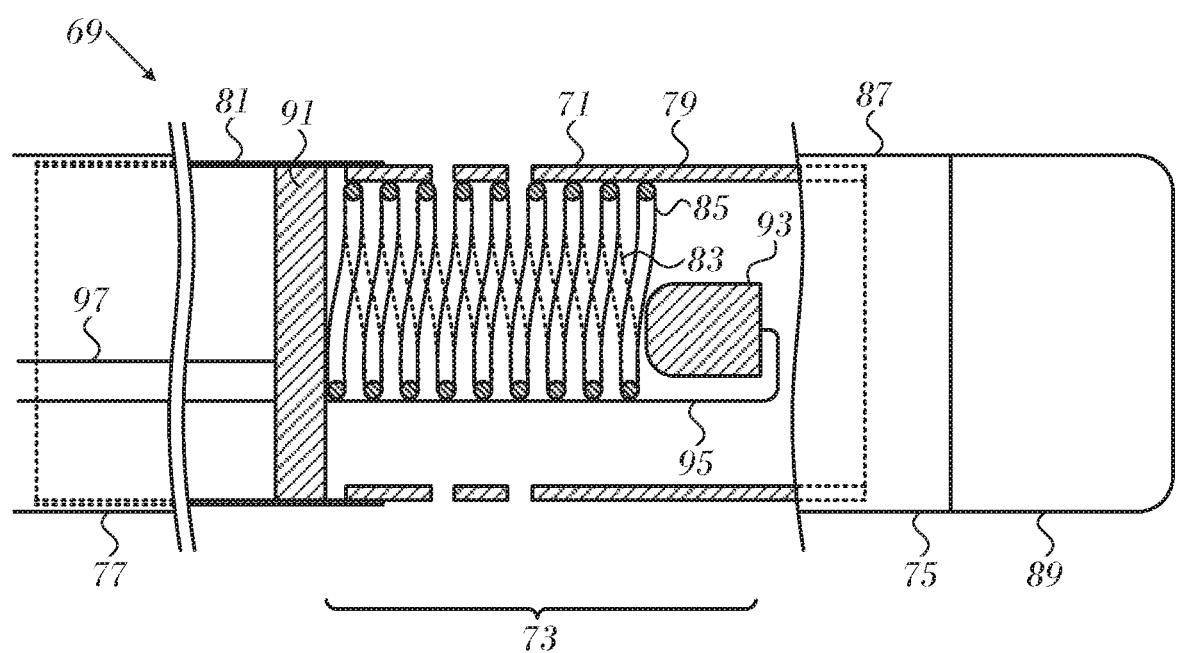
FIG. 3 is a schematic, sectional view showing details of the distal end of the catheter, in accordance with an embodiment of the invention.

Reference is now made to FIG. 3, which is a schematic, sectional view of the distal end of a catheter in accordance with an embodiment of the invention. A coupling member 71 forms a joint 73 between distal tip 75 and the distal end of insertion tube 77. By way of example, coupling member 71 is assumed to be formed in two parts, a first part 79 and a second part 81, the two parts being fixedly joined together. The two parts of coupling member 71 are generally tubular, and are joined so that the coupling member also has a tubular form. Although there is no necessity that coupling member 71 be formed of two parts, the two part implementation simplifies assembly of a magnetic field generator and magnetic position sensor into the member. The two part implementation is typically also facilitated by incorporating an attaching stem (not shown) into one of the parts.

Coupling member 71 has a one spring or a plurality of intertwined helical springs cut along a portion of the length of first part 79 of the member. The plurality of helices may comprise any integral number of single helices greater than one, such as, but not limited to two, three or four helices. For simplicity, unless otherwise stated, in the following description the plurality is assumed to comprise two intertwined single cut helices, a first cut helix 83 and a second cut helix 85, and is also referred to herein as a double helix. Those having ordinary skill in the art will be able to adapt the description without undue experimentation to encompass a plurality of intertwined helices where the plurality is more than two single helices.

Coupling member 71 (along with the distal end of catheter 69 generally) is typically covered by a flexible plastic sheath 87. When catheter 69 is used, for example, in ablating endocardial tissue by delivering radio-frequency electrical energy through electrode 89, considerable heat is generated in the area of distal tip 75. For this reason, it is desirable that sheath 87 comprises a heat-resistant plastic material, such as polyurethane, whose shape and elasticity are not substantially affected by exposure to the heat.

As noted above, catheter 69 comprises a transmitter 91 and a position sensor 93 within a distal portion of first part 79. The distal portion of the first part is located within distal tip 75. The position sensor 93 and the transmitter 91 are connected via conductors 95, 97, respectively, to a processing unit at the proximal end of insertion tube 77, typically in the console 24 (FIG. 1). Position sensor 93 is configured to sense the position of the distal tip relative to the distal end of insertion tube 77. As explained above, the position changes in response to deformation of the coupling member, and the processing unit may thus use the position reading in order to give an indication of the pressure exerted on and by the distal tip. A fuller description of a force sensor using these components is given in commonly assigned U.S. Patent Application Publications No. 2011/0130648 and 2009/0093806, which are herein incorporated by reference.

Figure 4:
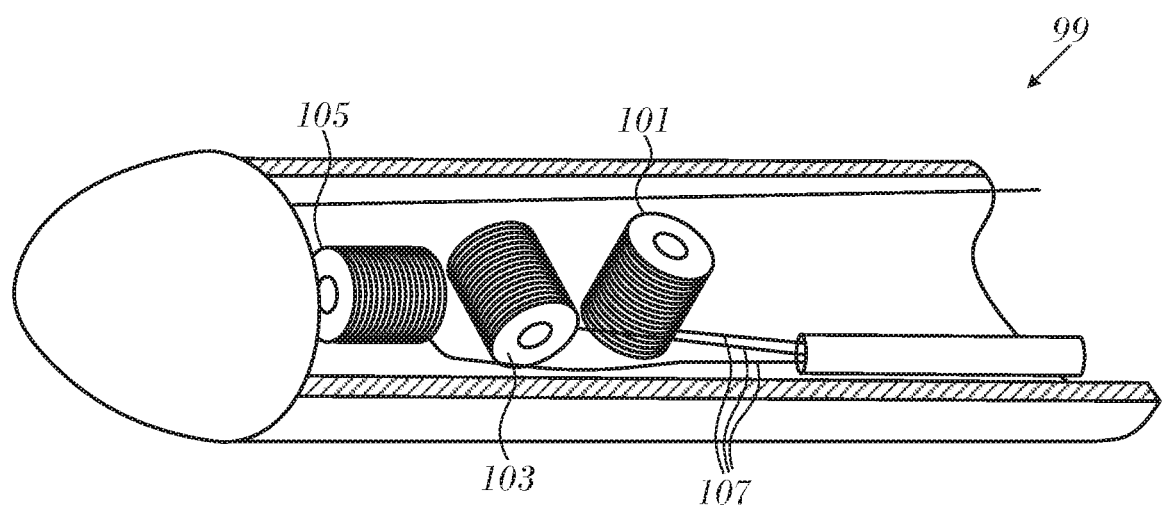
FIG. 4 is a graphical illustration of a receiver suitable for use in the catheter shown in FIG. 3 in accordance with an embodiment of the invention.

Reference is now made to FIG. 4, which is a graphical illustration of a receiver 99 that is suitable for use as the receiver 59 (FIG. 2), in accordance with an embodiment of the invention. The receiver 99 preferably includes two or more and more preferably three sensor coils 101, 103, 105 wound on air cores. The coils have mutually orthogonal axes. The coil 105 is conveniently aligned with the long axis of the catheter. The coils 101, 103, 105 are closely spaced along the axis of the catheter to reduce the diameter of the locating sensor and thus make the sensor suitable for incorporation into a catheter.

For most applications, quantitative measurement of the position and orientation of the catheter distal end relative to a reference frame is necessary. This requires at least two non-overlapping radiators that generate at least two distinguishable AC magnetic fields, the radiators' respective positions and orientations relative to the reference frame being known; a radiator driver, which preferably continuously supplies the radiators with AC signals to generate the AC magnetic fields; and a location sensor, consisting of at least two non-parallel sensors to measure the magnetic field flux resulting from the at least two distinguishable magnetic fields. The number of radiators times the number of sensors is equal to or greater than the number of degrees of freedom of the desired quantitative measurement of the position and orientation of the sensors relative to the reference frame. When it is desired to determine six position and orientation coordinates of the distal tip of the catheter, at least two coils are required in the receiver 99. Preferably three coils are used to improve the accuracy and reliability of the position measurement. In some applications where fewer dimensions are required, only a single coil oriented orthogonal to the axis of dipole emission by the transmitter may be necessary in the receiver 99.

Leads 107 are used to carry signals detected by the sensor coils 101, 103, 105 to a signal processor via the proximal end of the catheter, for processing to generate the required position information. Preferably, the leads 107 are twisted pairs to reduce pick-up and may be further electrically shielded. Further details of the operation of the receiver 99 are disclosed in PCT Patent Document WO96105768 of Ben Haim, which is herein incorporated by reference.

Operation.

Reverting to FIG. 2, ablation is optimally performed when the annular portion 49 of the ablator is in firm contact with and flush against the target tissue. In this situation there is no asymmetrical force on the tip of the catheter, although there is generally a force parallel to the axis of symmetry 51. The spring 63 is in a resting position and the longitudinal axis 67 is aligned with the axis of symmetry 51 as shown in FIG. 2.

Figure 5:
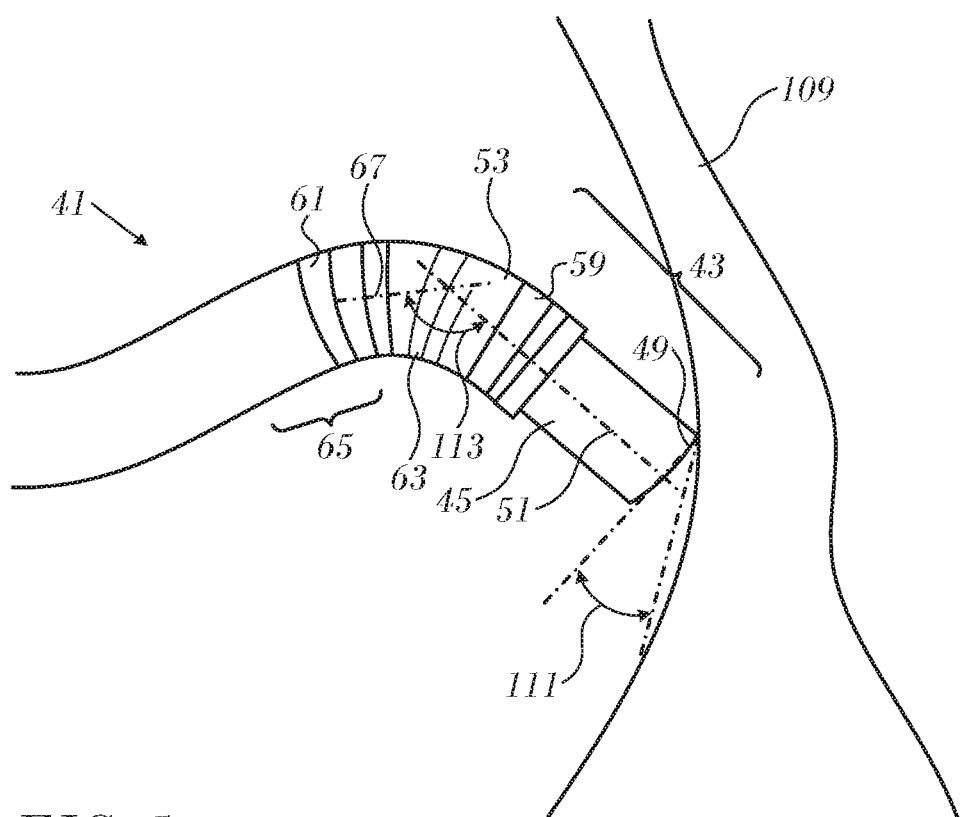
FIG. 5 is a graphical illustration of the distal portion of a catheter in an operating position in accordance with an embodiment of the invention.

Reference is now made to FIG. 5, which is a graphical illustration of the distal portion 41, shown in an operating position in accordance with an embodiment of the invention. The ablation electrode 45 is being forced into contact with intra-atrial septum 109. However the contacting force is asymmetric, causing the spring 63 of the contact force sensor 53 to flex. The annular portion 49 is not flush against the septum 109, but is incident with the septum 109 at an angle 111. The axis of symmetry 51 and the longitudinal axis 67 are not aligned, but meet at an angle 113- In this position analysis of the readings of the receiver 59 using the external field generating coils 28 (FIG. 1) in accordance with the teachings of the above-noted PCT Patent Document WO96105768 locates end portion 43 of the distal portion 41 of the catheter.

Operating the transmitter 61 at a different frequency than those used by the field generating coils 28 enables the processor 22 (FIG. 1) to determine the angular deflection of the end portion 43 with respect to the proximal portion 65, from which the contact force, and the magnitude of non-alignment with the proximal portion 65 may be computed as explained in the above-noted U.S. Patent Application Publications No. 2011/0130648 and 2009/0093806. Because of the axial symmetry of the field generated by a coil, in the embodiment of FIG. 5 only the magnitude of the deflection, i.e., the angle 113, can be computed using a single coil in the transmitter 61. However, by summing the orientation of the receiver that was obtained using the field generating coils 28 and the angular deflection, it is a straightforward matter for the processor 22 (FIG. 1) to derive the 3-dimensional orientation of the transducer, and hence the direction of beam emitted by the transducer. The transducer direction can be improved by calibrating the beam relative to the position sensor orientation.

The processor 22 (FIG. 1) may be configured to report when the end portion 43 is in alignment with the proximal portion 65, Optionally, the processor may then actuate the transducer in order to determine the tissue thickness.

Figure 6:
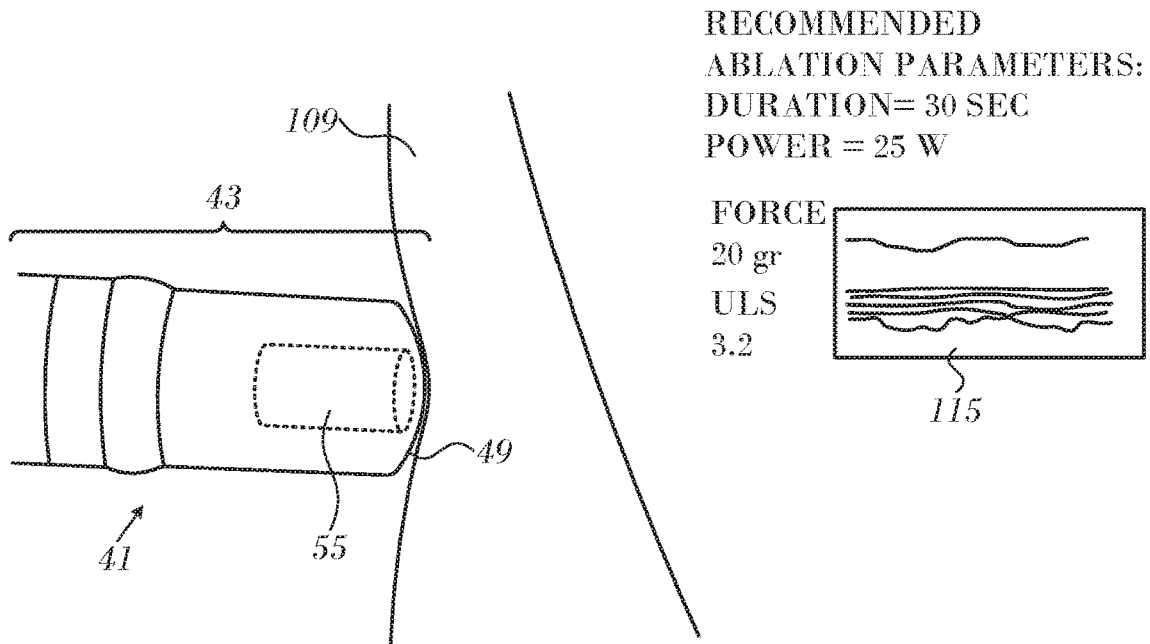
FIG. 6 is a graphical illustration of the distal portion of a catheter in an operating position in accordance with an embodiment of the invention.

Reference is now made to FIG. 6, which is a graphical illustration of end portion 43 shown in an operating position in accordance with an embodiment of the invention. The end portion 43 is essentially orthogonal to the septum 109, and the annular portion 49 is flush against septum 109, its contact force and orientation having been adjusted according to information obtained as described above. Ultrasonic transducer 55 has been pulsed activated in A-mode, in which it transmits and receives pulses of ultrasound energy. Echoes obtained in this manner from the septum 109 are processed by conventional image processing circuitry, which can be located in the console 24 (FIG. 1). As is well-known in the art, the thickness of tissue contacted by the ultrasonic transducer 55 is determined simply from the time of flight of the ultrasonic pulses. A graphical display 115 of the time-varying echogram obtained from the ultrasonic transducer 55 and contact force sensor 53 (seen in FIG. 2) is shown at the right of FIG. 6. The parameters shown in FIG. 6 can be determined by the processor 22 (FIG. 1) using an ablation index calculated as a product: constant*contact force*power*time. This index is highly correlated with the tissue thickness. Use of the factors in the index is described in commonly assigned U.S. Patent Application Publication No. 20140100563 by Govari, which is herein incorporated by reference.

Figure 7:
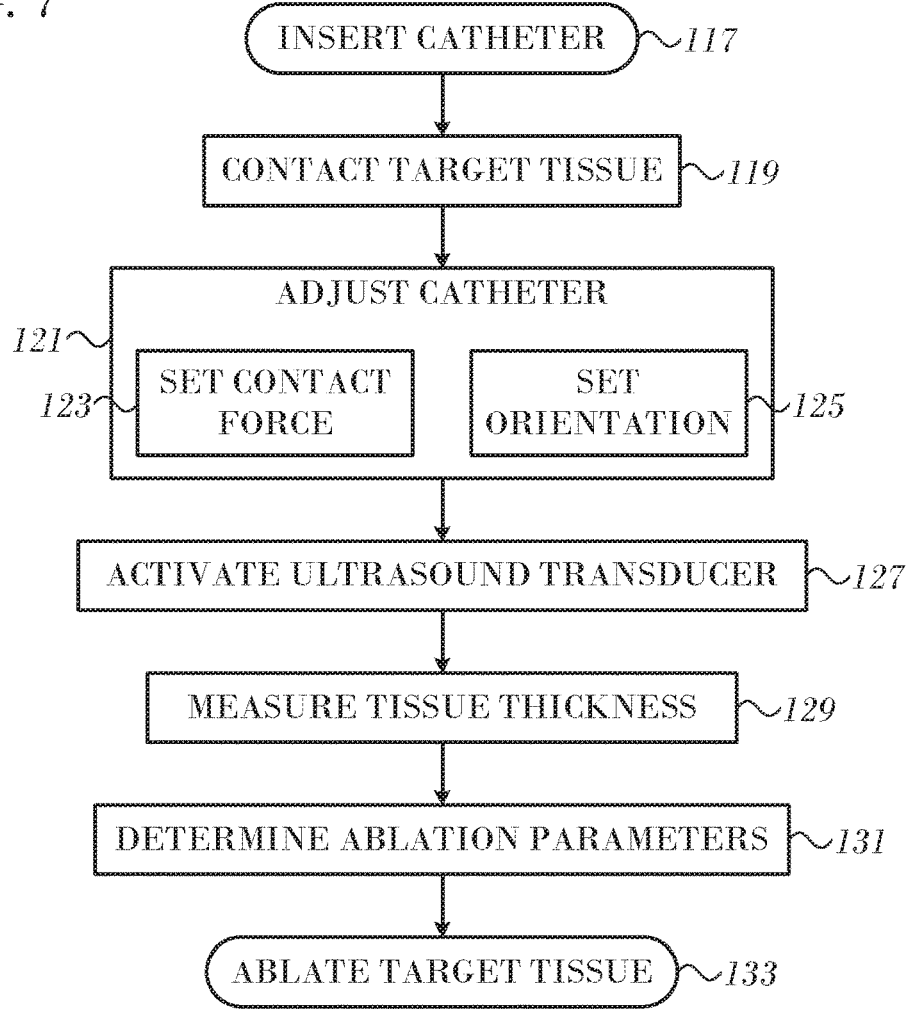
FIG. 7 is a flow chart of a method of catheterization in accordance with an embodiment of the invention.

Reference is now made to FIG. 7, which is a flow chart of a method of catheterization, in accordance with an embodiment of the invention. The method is explained with reference to the heart, but is applicable to other hollow viscera of the body. The process steps are shown in a particular linear sequence in FIG. 7 for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 117 a catheter having the features described in FIG. 2 is positioned in a cardiac chamber using conventional catheterization techniques.

Then, at step 119 contact is established between the tip of the catheter and the target tissue.

Next, at step 121 the tip of the catheter is aligned with the target tissue at a desired contact force. The force sensor measures both the magnitude of the force exerted by the probe, as well as the direction of the force with respect to the probe axis. Step 121 comprises step 123 in which contact force is adjusted to a desired level and step 125, in which the orientation of the tip is adjusted using the readings of receiver 59 of signals from the transmitter 61 (FIG. 2) such that the direction of force is orthogonal to the surface of the target tissue. Step 121, 123 may be coordinated by the operator. Once completed, the tip of the catheter and the direction of emissions of the ultrasound transducer are orthogonal to the surface of the target tissue. Moreover, the annular surface of the ablation electrode is optimally applied to the tissue surface.

Next, at step 127 the ultrasound transducer is activated in A-mode.

Next, at step 129 thickness of the target tissue and the depth of certain internal structures are derived from the times of flight obtained from the ultrasound transducer and its processing circuitry.

Next, at step 131 ablation parameters, i.e., the intensity and duration of the ablation energy, are determined using the information obtained in step 129. The details of this step are known in the art but are not repeated here, as they are outside the scope of this disclosure. The quality of a lesion generated in an ablation procedure depends on the force and the radio-frequency power being applied to the tissue being ablated, as well as on the thickness of the tissue being ablated and the duration of the ablation.

Then in final step 133 ablation of the target tissue may occur according to the requirements of the medical procedure. This can be accomplished using the ablation parameters determined in step 131. Optionally, temperature sensors, e.g., temperature sensor 57 (FIG. 2), may be used to monitor progress of the ablation.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:

contacting a flexible probe with target tissue in a cavity wall in a body of a subject, the flexible probe having a proximal portion, a distal end having a longitudinal axis, a distal segment having a tip centered about an axis of symmetry and an ablation electrode disposed on the tip, the ablation electrode having annular portion centered about the axis of symmetry, a resilient contact force sensor in the distal segment, a transmitter disposed within the flexible probe, a receiver disposed within the flexible probe and configured for receiving signals from the transmitter for sensing a position of the tip relative to the distal end, and an ultrasound transducer in the distal segment configured to direct ultrasonic energy parallel to the axis of symmetry toward the cavity wall;

adjusting a contact force between the flexible probe and the target tissue in response to readings of the resilient contact force sensor;

determining the position of the distal segment relative to the target tissue in response to readings from the receiver;

determining an angle of deflection between the axis of symmetry of the tip and the longitudinal axis of the distal end in response to the adjusted contact force between the flexible probe and the target tissue based on the signals received by the receiver from the transmitter;

deriving an orientation of the ultrasound transducer and direction of the ultrasonic energy to be emitted from the ultrasound transducer relative to the target tissue based on the determined position of the distal segment and the angle of deflection;

aligning the axis of symmetry of the tip and the longitudinal axis of the distal end in response to the derived orientation of the ultrasound transducer thereby causing the distal segment to be positioned orthogonally to the target tissue and the annular portion of the ablation electrode to be flush with the target tissue such that the ultrasound transducer will emit ultrasonic energy orthogonally to the target tissue when activated; and causing an alert to be generated when the axis of symmetry of the tip and the longitudinal axis of the distal end are aligned.

2. The method according to claim 1, wherein the resilient contact force sensor is disposed between the transmitter and the receiver.

3. The method according to claim 1, wherein the transmitter is a single frequency radiofrequency transmitter and the receiver comprises a single receiving coil.

4. The method according to claim 1, wherein the resilient contact force sensor forms a joint between a proximal portion of the flexible probe and the tip of the distal segment.

5. The method according to claim 1, wherein orienting the ultrasound transducer is performed while maintaining the desired contact force.

6. The method according to claim 1, further comprising activating the ultrasound transducer to emit ultrasound signals after orienting the ultrasound transducer.

7. The method according to claim 6, further comprising processing echo signals returning from the emitted ultrasound signals to determine a structure of the target tissue.

8. The method according to claim 7, wherein determining a structure of the target tissue comprises determining a thickness of the wall of the cavity.

9. The method according to claim 7, further comprising:
  determining ablation parameters in response to the determined structure of the target tissue; and
  activating the ablation electrode according to the ablation parameters to ablate the target tissue.

\* \* \* \* \*